US007906334B2

(12) United States Patent
Denchev et al.

(10) Patent No.: US 7,906,334 B2
(45) Date of Patent: Mar. 15, 2011

(54) METHOD FOR REPRODUCING CONIFERS BY SOMATIC EMBRYOGENESIS USING LACTOSE AS A CARBON SOURCE

(75) Inventors: Plamen Denchev, Victoria (CA); Stephen M. Attree, Victoria (CA); Lisheng Kong, Victoria (CA); Chia-Jung Tsai, Victoria (CA); Reed A. Radley, Vancouver (CA); Irina I. Lobatcheva, Victoria (CA)

(73) Assignee: Cellfor Inc., Saanichton, British Columbia (CA)

( * ) Notice: Subject to any disclaimer, the term of this patent is extended or adjusted under 35 U.S.C. 154(b) by 1102 days.

(21) Appl. No.: 10/764,978

(22) Filed: Jan. 23, 2004

(65) Prior Publication Data
US 2004/0203150 A1 Oct. 14, 2004

Related U.S. Application Data

(60) Provisional application No. 60/442,107, filed on Jan. 23, 2003.

(51) Int. Cl.
*C12N 5/00* (2006.01)
(52) U.S. Cl. .............. 435/422; 435/430.1; 435/430
(58) Field of Classification Search .............. 435/4, 422, 435/430.1, 430
See application file for complete search history.

(56) References Cited

U.S. PATENT DOCUMENTS

| | | | |
|---|---|---|---|
| 5,036,007 A | 7/1991 | Gupta et al. | |
| 5,187,092 A * | 2/1993 | Uddin | 435/422 |
| 5,482,857 A | 1/1996 | Gupta et al. | |
| 5,491,090 A * | 2/1996 | Handley et al. | 435/422 |
| 5,534,433 A * | 7/1996 | Coke | 435/431 |
| 6,492,174 B1 * | 12/2002 | Pullman et al. | 435/422 |
| 6,627,441 B1 * | 9/2003 | Attree | 435/422 |
| 6,689,609 B1 * | 2/2004 | Fan et al. | 435/422 |
| 6,897,065 B1 * | 5/2005 | Find | 435/422 |

FOREIGN PATENT DOCUMENTS
WO    WO 95/05070    2/1995

OTHER PUBLICATIONS

Dodds et al. Experiments in Plant Tissue Culture, 1985, 2nd ed., p. 41.*
Mantell et al. Principles of Plant Biotechnology an Introduction to Genetic Engineering in Plants, 1985, pp. 141-143.*
Von Arnold. Improved Efficiency of somatic embryogenesis in mature embryos of *Picea abies* (L.) Karst. 1987, J. Plant. Physiol., vol. 128, pp. 233-244.*
Vuke et al. Growth of loblolly pine callus on a variety of carbohydrate sources, 1987, Plant Cell Reports, 6(2), pp. 153-156.*
Schuller et al. Interaction of plant growth regulators and organic C and N components in the formation and maturation of *Abies alba* somatic embryos. Plant, Cell, Tissue and Organ Culture 60: 21-31, 2000.*
Schulz et al. Utilization of lactose in non-respiring cells of the yeast Debaryomyces polymorphus. Arch Microbiol (1986) 145: 367-371.*
Xianghui et al. Utilization in vitro of D-lactose by B6S3 tumor cells of tobacco. Plant Science Letters, vol. 21,issue 3, 1981, abstract only.*
Lactose 2010. Retrieved from the Internet at <http://en.wikipedia.org/wiki/Lactose> retrieved on Dec. 13, 2010, 3 pages.*
Galatose 2010. Retrieved from the Internet at <http://en.wikipedia.org/wiki/Galactose> retrieved on Dec. 13, 2010, 4 pages.*
Schuller et al., "Response of *Albies alba* Embryonal-suspensor Mass to Various Carbohydrate Treatments" *Plant Cell Reports* vol. 12, No. 4, pp. 199-202 (1993).
Attree SM, Pomeroy MK, and LC (Apr. 1995) "Development of White spruce (*Picea glauca*) somatic embryos during culture with abscisic acid and osmoticum, and their tolerance to drying and storage." J. Exp. Bot. 46(4): 433-439.
Attree SM, Fowke, LC (Oct. 1993) "Embryogeny of gymnosperms: advances in synthetic seed technology of conifers." Plant Cell, Tissue and Organ Culture 35(1):1-35.
Chandler S., Young R. (1995) "Somatic embryogenesis in *Pinus radiata*." Somatic Embryogenesis in Woody Plants, vol. 3, Gymnosperms (eds. S.M. Jain, P.K. Gupta and R.J. Newton) Dordrecht: Kluwer Academic Press, pp. 244-260.
Filonova LH, Bozhkov PV, von Arnold S. (Feb. 2000) "Developmental pathway of somatic embryogenesis in *Picea abies* as revealed by time-lapse tracking." J. Exp. Bot. 51(343):249-264.
Garin E., Plourde I. (Nov. 1998) "Screening of large numbers of seed families of *Pinus strobus* L. for somatic embryogenesis from immature and mature zygotic embryos." Plant Cell Reports 18(1-2):37-43.
Klimaszewska K., Smith DR (1997) "Maturation of somatic embryos of *Pinus strobus* is promoted by a high concentration of gellam gum." Physiol. Plant 100(4):949-957.
Laine E., David A. (1990) "Somatic embryogenesis in immature embryos and protoplasts of *Pinus caribaea*." Plant Sci. 69:215-224.
Lelu MA, Bastien C., Drugeault A., Gouez ML., Klimaszewska K. (Apr. 1999) "Somatic embryogenesis and plantlet development in *Pinus sylvestris* and *Pinus pinaster* on medium with and without growth regulators." Physiologia Plantarum 105(4):719-728.
Lipavská H., Konradová H. (Jan. 2004) "Invited Review: Somatic embryogenesis in conifers: the role of carbohydrate metabolism", In Vitro Cellular and Developmental Biology—Plant 40(1):23-30.
Ramarosandratana A., Harvengt L., Bouvet A., Calvayrac R., Paques M. (Jan. 2001) "Effects of carbohydrate source, polyethylene glycol and gellan gum concentration on embryonal-suspensor mass (ESM) proliferation and maturation of maritime pine somatic embryos." In Vitro Cellular and Developmental Biology—Plant 37(1):29-34.
Saborio F., Dvorak W., Donahue J., Torpe T. (Dec. 1997) "In vitro regeneration of plantlets from mature embryos of *Pinus ayacahuite*." Tree Physiol. 17(12):786-796.
Salajova T., Salaj J., Jasik J., Komutak A. (1995) "Somatic embryogenesis in *Pinus nigra*." Somatic Embryogenesis in Woody Plants, vol. 3, Gymnosperms (eds. S.M. Jain, P.K. Gupta and R.J. Newton) Dordrecht: Kluwer Academic Press, pp. 207-220.
Stange C. Prehn D., Gebauer M., Arce-Johnson P. (1999) "Optimization of in vitro culture conditions for *Pinus radiata* embryos and histological characterization of regenerated shoots." Biol Res 32:19-28.
Svobodova H., Albrechtova J., Kumstyrova L., Lipavaska L., Vagner M., Vondrakova Z. (Mar. 1999) "Somatic embryogenesis in Norway spruce: Anatomical study of embryo development and influence of polyethylene glycol on maturation process." Plant physiol. Biochem. 37(3):209-221.

* cited by examiner

*Primary Examiner* — June Hwu
(74) *Attorney, Agent, or Firm* — Michael Best & Friedich LLP (57) ABSTRACT

A method for reproducing conifers by somatic embryogenesis is disclosed. A galactose-containing compound is used as a carbon source for an embryogenic culture during at least one of the steps of induction, proliferation, and prematuration.

29 Claims, 6 Drawing Sheets

Fig. 1
Sucrose utilization after 7-day culture period

Fig. 2
Average growth rate during the 7-day culture period

Fig. 3
Average growth rate during preculture I stage

Fig. 4
Average growth rate during preculture II stage

Fig. 5
Lactose utilization at preculture I stage

Fig. 6
Lactose utilization at preculture II stage

METHOD FOR REPRODUCING CONIFERS BY SOMATIC EMBRYOGENESIS USING LACTOSE AS A CARBON SOURCE

CROSS REFERENCE TO RELATED APPLICATIONS

This application claims priority of U.S. Provisional Patent Application No. 60/442,107, filed Jan. 23, 2003, entitled "A METHOD FOR REPRODUCING CONIFERS BY SOMATIC EMBRYOGENESIS USING GALACTOSE CONTAINING COMPOUNDS AS A CARBON AND ENERGY SOURCE."

BACKGROUND OF THE INVENTION

Somatic embryogenesis offers the potential to clonally produce large numbers of plants of many species at low cost. Somatic embryos develop without the surrounding nutritive tissues and protective seed coat found with zygotic embryos, so research has been directed to causing somatic embryos to functionally mimic seeds with regard to efficient storage and handling qualities. The development of techniques for somatic embryogenesis in conifers has greatly improved the ability to culture conifer tissues in vitro and now offers the means to clonally propagate commercially valuable conifers. However, it is necessary to further reduce production costs to make somatic embryogenesis affordable to industry. Thus, there is a need in the technology for improvement of the efficiency of embryo production and of the quality and vigour of plants resulting from somatic embryos from all species of conifers.

BRIEF SUMMARY OF THE INVENTION

A method for reproducing conifers by somatic embryogenesis is disclosed wherein a galactose-containing compound is used as a carbon source for an embryogenic culture during at least one of the steps of induction, proliferation, and prematuration.

A method for reproducing conifers by somatic embryogenesis is disclosed wherein a galactose-containing compound at more than about 1% of the nutrient medium is used as a carbon source for an embryogenic culture during at least one of the steps of induction, proliferation, and prematuration.

A method for reproduction by somatic embryogenesis of *Pinus taeda* and hybrids, *Pinus radiata*, or *Pseudotsuga menziesii* is disclosed wherein a galactose-containing compound at more than about 1% of the nutrient medium is used during at least one of the steps of induction, proliferation, and prematuration.

DETAILED DESCRIPTION

The following definitions are those consistent with the usage of terms in the present specification.

Abscisic Acid (ABA) A plant growth regulator in the group of stress hormones.

Auxin A plant growth regulator which may be natural or synthetic. The main physiological effect of auxin is to stimulate cell elongation. Examples are indole acetic acid (IAA) and 2,4-dichlorophenoxyacetic acid (2,4-D).

Clone When used in the context of plant propagation, the term refers to a collection of individuals having the same genetic constitution (genotype), and is produced from a culture that arises from an individual explant.

Conversion The ability of a somatic embryo to germinate (either in vitro or ex vitro) and subsequently develop into an established, autotrophic plant with root and needles.

Cytokinin A natural or synthetic plant growth regulator such as benzyl adenine (BA). The main physiological effect of cytokinin is to stimulate meristematic cell division.

Desiccation The drying of an embryo by any means to a moisture content less than that of the original hydrated embryo. Desiccation processes may include (a) mild desiccation, which encompasses moisture contents in the 36-55% moisture content range, and (b) severe desiccation, which occurs at moisture contents less than 36%, usually in the range of about 5-30%. A severely desiccated viable embryo is able to survive freezing, and after rehydration, is able to successfully complete the germination process and convert to a normal autotrophic plant.

Embryogenic culture A plant cell or tissue culture capable of forming somatic embryos and regenerating plants via somatic embryogenesis.

Explant Organs, tissues or cells derived from a plant and cultured in vitro for the purposes of starting a plant cell or tissue culture.

Galactose A hexose of the formula $CH_2OH.(CHOH)_4CHO$. It is present in certain gums and seaweeds as a polysaccharide galactan and as a normal constituent of milk.

Lactose Lactose is a disaccharide ($C_{12}H_{22}O_{11}$). It yields D-glucose and D-galactose on hydrolysis, which is catalysed by lactase.

Line This is another term for "clone".

Mature embryo A mature embryo is one which is capable of germination to yield a seedling with shoot and root, given the necessary environmental conditions (temperature, light, water, nutrients, etc.). The term implies that the embryo has undergone development through various developmental stages and has reached a size and stage suitable for germination. The embryo contains storage proteins, lipids, and if provided with suitable maturation conditions (e.g. ABA and water stress), will be desiccation tolerant, so may be desiccated prior to germination.

Megagametophyte A haploid nutritive tissue of gymnosperm seed, of maternal origin, within which the gymnosperm zygotic embryos develop.

Moisture content The amount of water present in an embryo. This is generally measured by weighing an embryo before and after oven drying (FW and DW, respectively). The preferred manner of expression is percentage weight of water based on the original weight of the embryo, so that the values are always less than 100. $MC = ((FW-DW)/FW) \times 100\%$ Prematuration The step following the proliferation step and prior to the maturation step, usually involving a gradual reduction in the concentrations of one or more of the hormones auxin and cytokinin and/or a change in water stress and the addition of ABA.

Proliferation The steps following induction prior to maturation, in which embryogenic cultures divide and grow but do not develop into mature embryo stages. The proliferation step may also be referred to as the maintenance step.

Nutrients The inorganic micro- and macro-minerals, vitamins, hormones, organic supplements, and carbohydrates (or any one or more of them) necessary for culture growth and somatic embryo germination.

Somatic embryo A plant embryo formed in vitro from vegetative (somatic) cells by mitotic division of cells. Early stage somatic embryos are morphologically similar to immature zygotic embryos, and comprise a region of embryonal cells subtended by suspensor cells.

Somatic Embryogenesis A process of initiation and development of somatic embryos in vitro from somatic cells and tissues.

Water potential The total water potential to which an organism is subjected in a water-containing matrix. This is a sum of (1) osmotic (solute) potential, (2) gravitational potential resulting from the vertical position of the water, and (3) a suction component (capillary or matric potential).

Water Stressing The reduction of water potential to which an embryogenic tissue or somatic embryo is controlled during maturation by controlling the environment of the tissue or embryo in order to modify the progress of maturation.

Zygotic Embryo An embryo derived from the sexual fusion of gametic cells produced by meiosis.

Somatic embryogenesis in plants is a multistep process consisting of induction, proliferation, maturation (embryo development), and germination and requires that specific culture conditions, including nutrient media compositions, are provided for each step of the multistep process. Thus, in general for most conifers an auxin and cytokinin and a low osmoticum are required in media for induction and proliferation of embryogenic tissues. For further embryo development it is often beneficial to increase the osmotic concentration, and to replace the auxin and cytokinin with abscisic acid (ABA). The effects of different carbohydrates on the different steps of somatic embryogenesis are not clearly understood. For conifers the optimal carbohydrate has thus far been found to be either sucrose or maltose (Iraqi and Tremblay 2001 a, Iraqi and Temblay 2001b, Ramarosandratana et al, 2001).

Water stress plays an important role in maintaining embryos in a maturation state, and low water content rather than ABA may prevent precocious germination during later stages of development. This is important because precocious germination of embryos during development in seeds would be lethal during desiccation. A conventional way to water stress plant cells grown in vitro is to increase the osmotic concentration of the culture medium through the use of plasmolysing osmotica. For example, increased concentrations of plasmolysing osmotica such as sucrose or mannitol have been used to promote somatic embryo maturation of many plant species.

Sucrose or maltose are considered to be the most suitable carbon sources for conifers, depending upon the species, for most stages of culture. Lactose has been used as an osmoticum with maltose or sucrose supplements as the carbon source during the conifer maturation step. Lactose or galactose has not been described as a suitable energy source for the induction or maintenance of the immature embryo stages. The newly-discovered fact that embryos of some conifer species can hydrolyze lactose and/or metabolize galactose at certain developmental stages without galactose toxicity, and that this results in improved cultures is an unexpected beneficial result.

Here, a compound containing galactose as a carbon and energy source in the media is used during early conifer embryogenesis, specifically sugars containing galactose or galactose subunits. The most suitable sugars are galactose or lactose, the choice of which depends on the conifer species being cultured.

The method is especially well suited to culturing conifers of the family Pinaceae, especially those species including *Pinus taeda* (loblolly pine), *Pinus radiata* (radiata pine) and *Pseudotsuga menziesii* (Douglas fir). The method produces higher induction frequencies.

The method promotes differentiation of immature embryos in proliferation cultures. These embryos when subsequently transferred to development (maturation) medium show reduced growth of suspensor tissue, improved embryo quality and improved yields of mature embryos. This results in higher numbers of genotypes that can be successfully cultured and cryostored, and results in a higher number of seedlings produced at lower costs than those of prior known methods.

Diploid cultures of conifers are most readily initiated from zygotic embryos, which are genetically dissimilar from each other. Low osmotic conditions are beneficial for induction from conifers. The sugar most often used for induction is sucrose at about 1% (w/v) concentration. However, the use of galactose-containing compounds, such as galactose and lactose at the induction stage, is now shown to lead to improved induction success. The most suitable concentration may be less than about 6%, and, more particularly, may be less than about 2%, and even more particularly, between about 1% and about 2%, alone or with additional carbon sources. Cytokinin is important to most species, and is usually included with an auxin at concentrations of 5 and 10 µM, respectively.

Exceptions to the above plant growth regulator (PGR) requirements are *Abies* spp, which are different from other conifers, and require cytokinin as the sole PGR for induction as well as proliferation.

Genotype specificity for embryogenic induction occurs in conifers. Also, the induction of somatic embryogenesis is under strong additive genetic control. For conifers, immature zygotic embryos yield somatic embryos more readily than mature zygotic embryos, which are generally more responsive than explants from young seedlings. Cryopreservation of immature somatic embryos in liquid nitrogen is routine for long-term preservation and is used to preserve genotypes while extended field tests are carried out. Following the field trials elite genotypes are then removed from cryogenic storage and bulked up in liquid suspensions for mass propagation. Methods of this invention lead to greater numbers of cryopreserved lines following induction.

Embryogenic cultures of conifers are usually maintained on a medium similar to the induction medium, which typically includes an auxin, a cytokinin and a low concentration of sugar. The method of maintenance (or proliferation) depends upon the intended use of the culture. A common way to maintain cultures is on semi-solidified medium in Petri dishes. These stationary cultures are sub-cultured every 2-4 weeks to prevent browning and death. Liquid culture is more suitable for maintaining conifer cultures in a rapidly proliferating state for large scale propagation.

Pine embryogenic tissue, when grown on abscisic acid (ABA) in the presence of sucrose, undergoes a disorganised growth phase, prior to organised growth. Such cultures do not readily undergo further development with ABA and a low osmotic concentration, perhaps because they are too juvenile to respond to ABA. Replacing the sucrose with lactose or galactose at the proliferation step has the benefit of reducing disorganised growth, and leads to the production of well-organised immature embryos with enlarged embryonal regions. This effect is more pronounced than with maltose. When transferred to maturation medium these lactose/galactose embryos have a greater propensity to develop to mature embryo stages than those grown on other sugars, including maltose, and disorganised suspensor tissue proliferation is inhibited. The result is that mature embryos are produced in higher yields than with other known methods, and the mature embryos are of greater uniformity. They are also of better quality and thus are vigorous during subsequent germination. All of the latter lead to greater numbers of plants recovered at the end of the process.

In order to encourage the production of mature developmental stages of conifer somatic embryos, immature somatic embryos must be transferred from a medium containing hormones to stimulate proliferation to an environment containing ABA and ideally a raised osmotic concentration. A gradual transition to these growth conditions is often beneficial. Thus, prior to ABA treatments, immature somatic embryos may be transferred to a prematuration medium containing no, or reduced, plant growth regulators. Charcoal may be beneficial.

Following the maturation step it is often desirable to desiccate the somatic embryos. A moisture content of less than 55% is beneficial to producing high storage reserves and inducing desiccation tolerance. In addition to promoting germination, desiccation reduces production costs by providing a means of storing somatic embryos. For optimal efficiency, mature somatic embryos can be produced continuously year round, then stored and pooled with somatic embryos from subsequent production runs. They can then be germinated synchronously to provide plants of uniform age and size for planting during a suitable growing season.

Post-germinative growth of conifer somatic embryos occurs without the benefit of the haploid megagametophyte, which is a major organ for storage of both lipids and proteins within the conifer seed. Conifer somatic embryos therefore require nutrients, usually in the form of PGR-free media supplied at half strength and containing 1-3% sucrose for further growth into autotrophic plants.

The process of the present invention is not limited to any single basal culture medium. Any well known medium or modification may be used, however we have found the formulation below to work well for many conifers as described in the following sections.

TABLE A

TX medium basal salts

| Basal salts | Amount per liter Medium, mg |
|---|---|
| Major | |
| $KNO_3$ | 950.00 |
| $KH_2PO_4$ | 170.00 |
| $MgSO_4 \cdot 7H_2O$ | 925.00 |
| $CaCl_2 \cdot 2H_2O$ | 211.00 |
| Minor | |
| KI | 4.15 |
| $H_3BO_3$ | 31.0000 |
| $ZnSO_4 \cdot 7H_2O$ | 43.0000 |
| $MnSO_4 \cdot H_2O$ | 21.0000 |

TABLE A-continued

TX medium basal salts

| Basal salts | Amount per liter Medium, mg |
|---|---|
| $Na_2MoO_4 \cdot 2H_2O$ | 1.5000 |
| $CuSO_4 \cdot 5H_2O$ | 0.5000 |
| $CoCl_2 \cdot 6H_2O$ | 0.1300 |
| Iron | |
| $FeSO_4 \cdot 7H_2O$ | 27.8 |
| $Na_2EDTA$ | 37.2 |
| Vitamins | |
| Thiamine-HCl | 0.1000 |
| Pyridoxine-HCl | 0.1000 |
| Nicotinic acid | 0.5000 |
| Myo-Inositol | 100 |

EXAMPLES

Examples Assessing Loblolly Pine Somatic Embryogenesis

Example 1

Effect of Carbon Source on Induction of Loblolly Pine

Female gametophytes containing the immature zygotic embryos were used as explants. The cones were surface sterilized in 10% bleach solution for 15 min. They were rinsed 3 times with sterile water, air dried and stored in polyethylene bags at 4° C. until used. Seeds were sterilized in 3% hydrogen peroxide containing 0.1% Tween 20 and rinsed in sterile deionized water. Megagametophytes containing the immature embryos were plated on TX medium (Table A) supplemented with 2.2 mg/l 2,4-D, 1 mg/l BA and 0.3% Phytagel and containing either 1% sucrose, or 1.5% lactose and 0.025% glucose.

Cultures were maintained on the two media by subculturing the embryogenic tissue every 10 to 14 days to fresh media. All cultures were incubated at 23° C. in the dark. The results of the induction are presented in Table 1.

TABLE 1

Effect of carbon source on Loblolly pine induction success

| Treatment | % induction |
|---|---|
| TX sucrose | 1.46 |
| TX lactose | 6.85 |

Induction success was greater than three times higher when medium containing lactose was used.

Example 2

Effect of Carbon Source on Solid Maintenance of Loblolly Pine

Tissue induced on sucrose from Example 1 was further maintained on the semi-solid TX medium containing 1% sucrose, and tissue induced on lactose was maintained on semi-solid TX medium containing 1.5% lactose and 0.025% glucose. The tissue morphology of the lines induced on lactose was different from the ones induced on sucrose. Tissue induced on lactose-containing medium consisted of more early-stage immature embryos and a limited amount of suspensor type of surrounding tissue. Predominantly suspensor type tissue and very few embryos were observed in the tissue induced on sucrose. In order to further increase the proliferation rate, 0.5% sucrose was added to the TX 1.5% lactose-containing medium in place of 0.025% glucose. This medium provided a reasonable bulk-up rate, and growth of embryos was more synchronized than in the 1% sucrose medium.

Example 3

Effect of Carbon Source on Liquid Maintenance

Suspension cultures of loblolly lines LP1, LP2, LP3, LP4 and LP5 were started with 2 g of tissue introduced to 50 ml of TX liquid medium containing different sugars—1% sucrose, 1.5% maltose, or 1.5% lactose. These cultures were maintained in the same liquid media for 2 weeks by weekly transfers to fresh maintenance medium containing the above sugars. Then, 2 g of tissue produced in each maintenance medium was transferred to prematuration media I, containing the same carbon source as the maintenance media. After one week, 1.5 g of tissue from each prematuration medium I was transferred to prematuration media II containing the same sugars. After the 4 week period in liquid media, early stage somatic embryos were collected and plated on ½ LV maturation medium containing 120 µM ABA and 6.0% sucrose and 1% Phytagel. Eight to ten weeks later, mature somatic embryos were counted and treatments were evaluated based on the number of somatic embryos per gram fresh weight (SE/g FW). Table 2 summarises the tissue yield at the end of the 4-week period and the number of mature somatic embryos produced for each line.

TABLE 2

Effect of carbon source on growth rate and yield of somatic embryos.

| Carbon source | Average amount of tissue produced after 4 weeks in liquid (FW g) | # SE/g FW ± sd |
|---|---|---|
| 1% Sucrose | 592.06 | 126 ± 20 |
| 1.5% Maltose | 204.45 | 209 ± 28 |
| 1.5% Lactose | 18.63 | 393 ± 10 |

The highest growth rate was observed when sucrose was used for the entire 4-week liquid period. The lowest amount of tissue was obtained when lactose was used as sole carbon source. However, tissue cultured in lactose-containing media produced the highest number of SE/g FW. This significantly reduces production costs, as about 60% less maturation cultures are required to produce a target number of embryos.

Example 4

Effect of Lactose During the Prematuration Steps

Prematuration for loblolly pine may be performed in two steps:
1. Prematuration I requires reduction of hormones either by reducing the auxin and cytokinin concentrations to optimally about 1/20 of the concentration of proliferation step, or by adding charcoal at about 0.01 to 1%, or a combination of both.
2. Prematuration II follows prematuration I and requires an addition of ABA at concentrations of about 5 to 120 µM, preferably 90 µM and no auxin and cytokinins.

In order to further understand the effect of lactose on somatic embryo development, liquid maintenance cultures were started in TX medium containing 1% sucrose as in Example 3. Three lines were used in this experiment, LP2, LP3 and LP4. After the proliferation step, 2 g of the tissue was transferred for one week to prematuration medium I containing different concentrations of lactose—1.5%, 3% and 6%. After that, 1.5 g of tissue produced in the lactose-containing media was further cultured for a week in prematuration medium II containing the same amount of lactose. The summary of the results is presented in Table. 3.

TABLE 3

Effect of lactose at the prematuration step.

| Carbon source | Mean grams FW at the end of prematuration stage | Mean # SE/g FW ± sd |
|---|---|---|
| 1% Sucrose to 1.5% lactose | 121.90 | 106 ± 9 |
| 1% Sucrose to 3% lactose | 216.47 | 209 ± 7 |
| 1% Sucrose to 6% lactose | 149.13 | 169 ± 10 |

The highest numbers of somatic embryos were obtained when 3% lactose was used for the last two weeks of the liquid prematuration step.

Example 5

Carbohydrate Metabolism

In order to understand the effect of sucrose and lactose on somatic embryo development, all media required for the liquid stage (maintenance, prematuration I and II) were analysed for sucrose, glucose, lactose, and galactose. Two lines were used in this experiment: LP3 and LP6.

Figure 1:
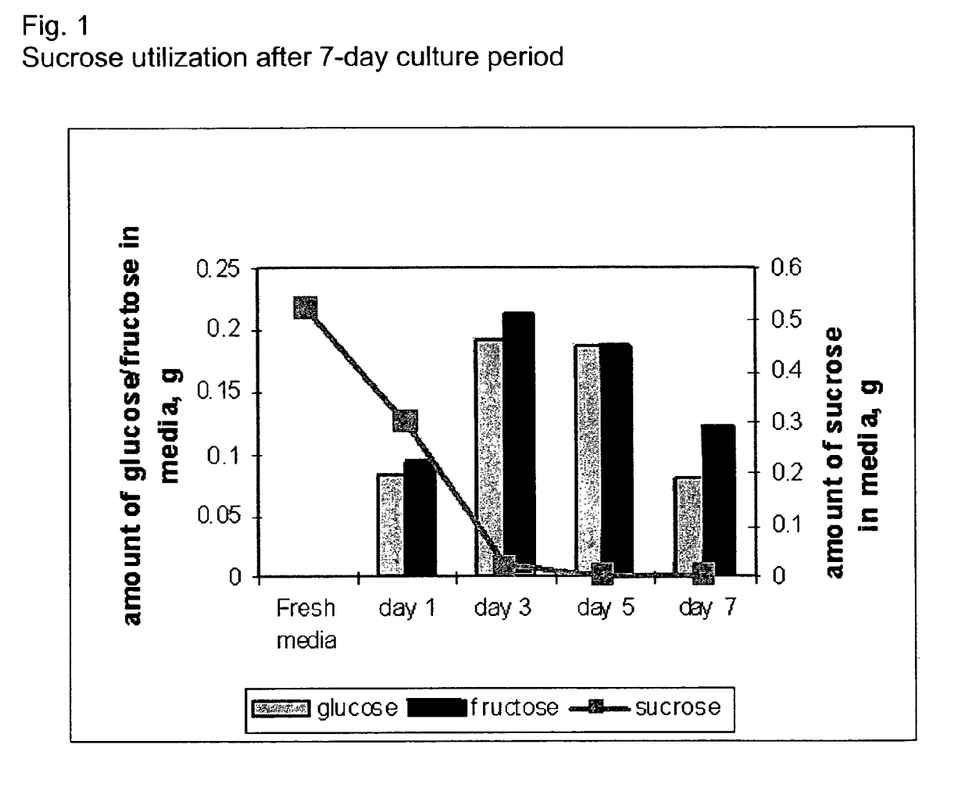
FIG. 1 represents the ability of loblolly pine lines grown on TX maintenance medium to hydrolyze sucrose over time.
Figure 2:
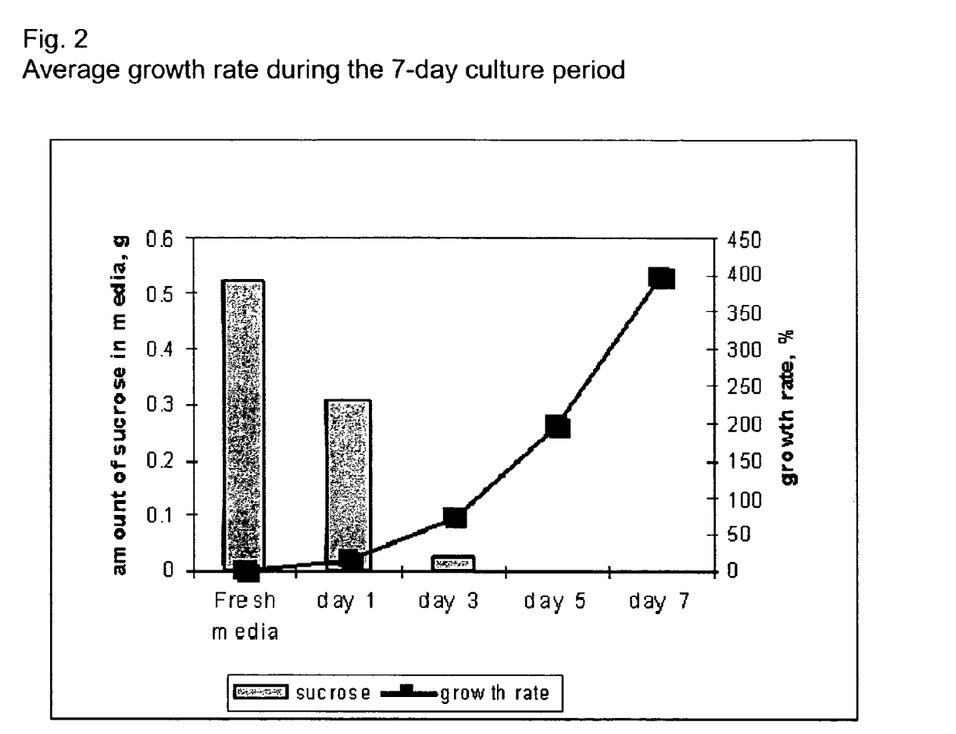
FIG. 2 represents the growth rate of loblolly pine lines grown on TX maintenance medium.

Both lines completely hydrolysed sucrose at day 5 during the first week of culture in TX maintenance medium. A similar pattern in the ability of the lines to hydrolyse sucrose was observed after transferring the tissue to the same medium for an additional week of culture. FIG. 1 represents an average of the results for both lines. The growth rates of the lines during the two-week period followed a similar pattern (FIG. 2). Line LP3, however, metabolised more glucose and at the end of the 2-week period no glucose was detectable in the medium. This same line produced the largest amount of tissue (1278.18 g) at the end of the 4 week-liquid period when sucrose was used as sole carbon source.

Figure 3:
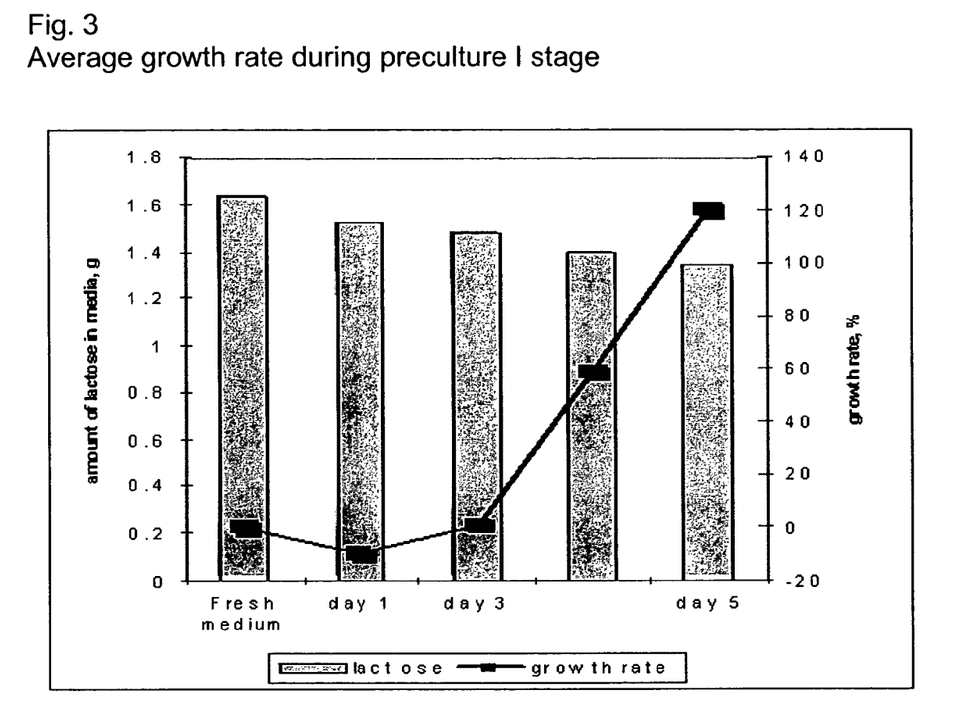
FIG. 3 represents the growth rate of loblolly pine lines grown on prematuration medium I containing lactose.
Figure 4:
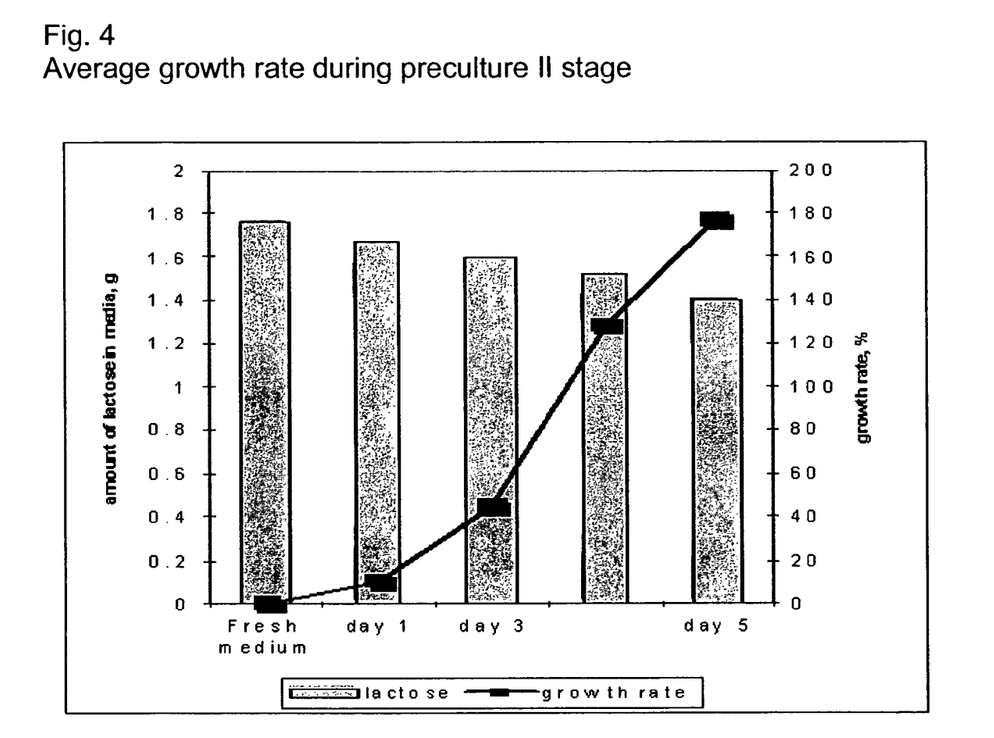
FIG. 4 represents the growth rate of loblolly pine lines grown on prematuration medium II containing lactose.
Figure 5:
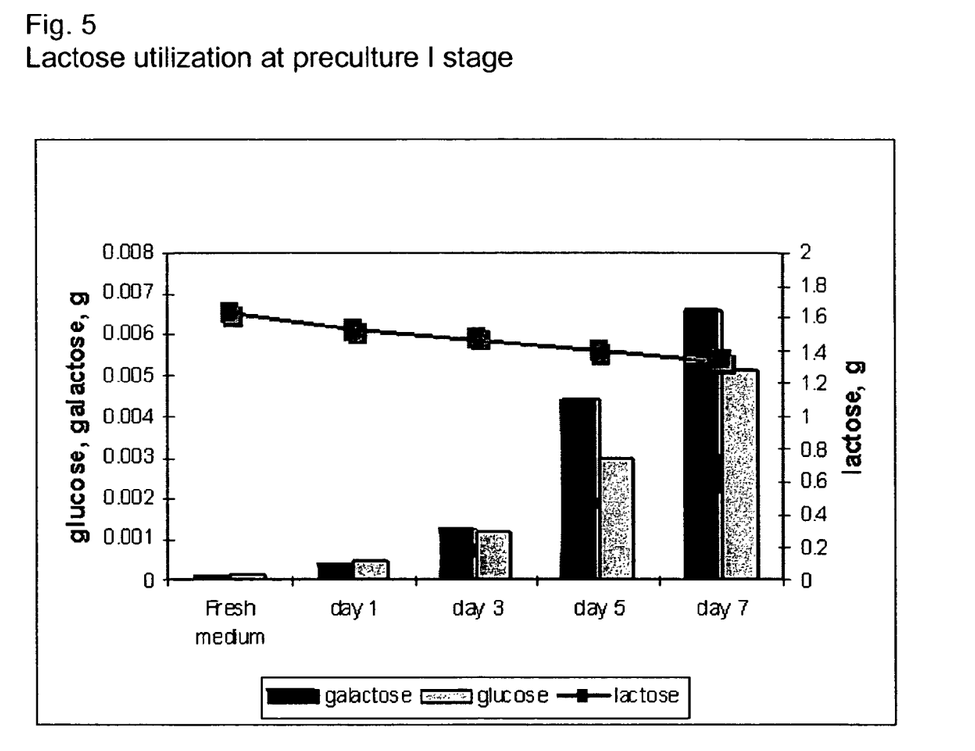
FIG. 5 represents the ability of loblolly pine lines grown on prematuration medium I and utilise lactose by breaking it down to produce glucose and galactose.
Figure 6:
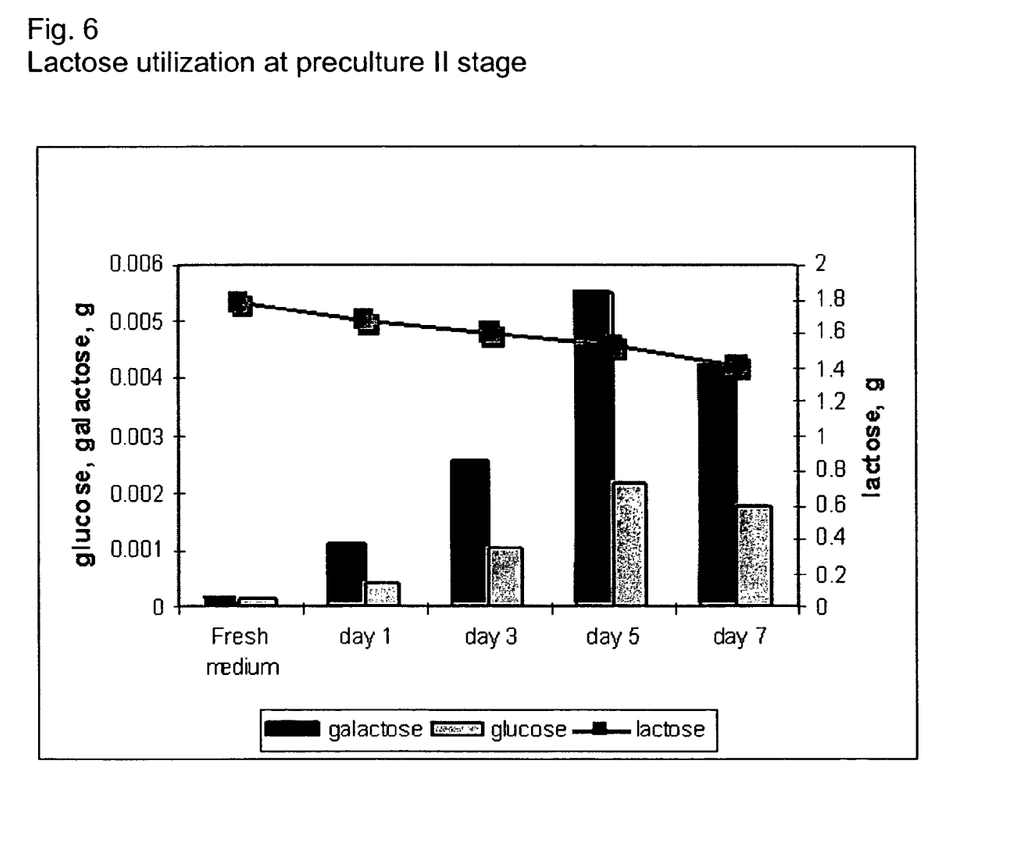
FIG. 6 represents the ability of loblolly pine lines grown on prematuration medium II to utilise lactose by breaking it down to produce glucose and galactose.

After transferring the tissue to the prematuration medium I containing lactose, both lines maintained a similar growth pattern (FIG. 3). During the second week in lactose, at the prematuration II stage, both lines showed a significant increase in the growth rates (FIG. 4). When media were analysed for the presence of glucose and galactose (FIGS. 5 and 6), detectable amounts of glucose and galactose were observed for both lines. A decrease of the amount of lactose was also detected. It is clear that both lines were capable of utilising lactose (Table 4). Data presented in FIG. 6 also provide grounds to conclude that the lines were not only capable of metabolising lactose but also of utilising galactose, as a significant amount of "missing" galactose was registered at day 7 in comparison to day 5 (where the glucose amounts in the medium were the same).

TABLE 4

Sugar utilisation summary

| Sugar | Amount of sugar in media at the start, % | % sugar missing (utilised) |
|---|---|---|
| Sucrose | 1.0 | 30 |
| Lactose | 1.5 | 12 |

Example 5.1

Effect of Galactose During Proliferation and Prematuration Steps on Loblolly Pine The finding that loblolly pine cultures were capable of utilising galactose is unique. In order to further investigate these phenomenon two lines, LP1 and LP3, were cultured on semi-solid TX medium containing 1.0% lactose and 0.5% sucrose. Cultures were maintained by subculturing the embryogenic tissue every 10 to 14 days to fresh media. All cultures were incubated at 23° C. in the dark. Suspension cultures were initiated as described in Example 3, however, TX medium was supplemented with either 1% sucrose, 1.5% maltose, 1.5% lactose, or 0.75% galactose. These cultures were maintained in liquid media for 4 weeks by weekly transfers to fresh maintenance or prematuration media. After the 4-week period, 1 ml of the liquid medium containing 0.1 g of tissue consisting of early stage somatic embryos was plated on each 10 mm plates containing ½ LV maturation medium. This medium contained 120 µM ABA and 6.0% sucrose and 1% Phytagel. Eight to ten weeks later, mature somatic embryos were counted and treatments were evaluated based on the number of somatic embryos per gram fresh weight (Table 5).

TABLE 5

Effect of galactose and galactose-containing sugars on SE yield

| Carbon source | Line | Amount of tissue at the end of the preculture II stage | # SE/g FW |
|---|---|---|---|
| Sucrose | LP1 | 121.22 | 11 ± 3 |
|  | LP3 | 1278.18 | 100 ± 6 |
| Maltose | LP1 | 232.18 | 106 ± 4 |
|  | LP3 | 118.22 | 160 ± 5 |
| Lactose | LP1 | 28.9 | 1060 ± 17 |
|  | LP3 | 8.78 | 110 ± 7 |
| Galactose | LP1 | 59.45 | 216 ± 8 |
|  | LP3 | 8.65 | 172 ± 5 |

The results show that all lines were able to produce mature embryos after culturing in sucrose medium. However, they performed differently when maltose, lactose or galactose was used as a carbon source. Line LP1 produced over 1000 embryos when cultured in lactose-containing TX medium and only 11 embryos when sucrose was used as a carbon source. Although a reduction in embryo yield was observed when the same line was cultured in galactose-containing TX media, the number of embryos produced by LP1 when galactose was used as the carbon source was significantly higher than the number obtained on sucrose- or maltose-containing TX media. Line LP3 produced more embryos after culturing in TX galactose-containing media. Again, the lowest embryo yield was observed when sucrose was used as carbon source. These results suggest that different lines require different types of sugar as a carbon source for their optimum performance, but galactose-containing sugars are superior.

Examples Assessing Radiata Pine Somatic Embryogenesis

Example 6

Effect of Carbon Source on Induction of Radiata Pine

Female gametophytes containing immature zygotic embryos were used as explants. The cones were surface sterilised in 10% bleach solution for 15 min. They were rinsed 3 times with sterile water, air dried and stored in polyethylene bags at 4° C. until used. Seeds were sterilised in 3% hydrogen peroxide containing 0.1% Tween 20 and rinsed in sterile deionized water. Megagametophytes containing the immature embryos were plated on MSG (standard radiata pine medium containing sucrose, Table B) and on TX medium (Table A) supplemented with 2.2 mg/l 2,4-D, 1 mg/l BA and 0.3% Phytagel and containing 1.5% galactose and 0.5% sucrose. Casein hydrolysate was reduced to 1000 mg/l (TXR medium).

TABLE B

MSG basal salts

| Basal salts | Amount per liter Medium, mg |
|---|---|
| Major | |
| $KNO_3$ | 100 |
| $KH_2PO_4$ | 170 |
| $MgSO_4 \cdot 7H_2O$ | 370 |
| $CaCl_2 \cdot 2H_2O$ | 440 |
| KCl | 745 |
| Minor | |
| KI | 0.83 |
| $H_3BO_3$ | 6.2 |
| $MnSO_4 \cdot H_2O$ | 16.9 |
| $ZnSO_4 \cdot 7H_2O$ | 8.6 |
| $Na_2MoO_4 \cdot 2H_2O$ | 0.25 |
| $CuSO_4 \cdot 5H_2O$ | 0.025 |
| $CoCl_2 \cdot 6H_2O$ | 0.025 |
| Iron | |
| $FeSO_4 \cdot 7H_2O$ | 27.8 |
| $Na_2EDTA$ | 37.3 |
| Vitamins | |
| Thiamine-HCl | 0.1 |
| Pyridoxine-HCl | 0.1 |
| Nicotinic acid | 0.5 |

Cultures were maintained on the two media by subculturing the embryogenic tissue every 10 to 14 days to fresh media. All cultures were incubated at 23° C. in the dark. Suspension cultures were initiated as 2 g of tissue were introduced to 50 ml of TXR liquid medium containing 1.0% sucrose. These cultures were maintained in liquid media for 40-48 days by transfers to fresh maintenance medium every 10 to 14 days.

One ml of TXR medium containing 0.1 g tissue consisting of early stage somatic embryos was plated on modified ½ LV maturation medium (Table C) in which glutamine was reduced to 500 mg/l and casein hydrolysate to 1000 mg/l. In addition, 120 µM ABA, 6.0% sucrose and 1% Phytagel were added. Twelve to fourteen weeks later, mature somatic embryos were counted and treatments were evaluated based on the number of somatic embryos per gram fresh weight.

The results of the induction are presented in Table 6. Induction success was greater than three times higher when galactose was used as a carbon source and subsequent yields of mature embryos from these tissues were almost double.

TABLE C

1/2 LV medium basal salts

| Basal salts | Amount per liter Medium, mg |
|---|---|
| Major | |
| NH$_4$NO$_3$ | 825.00 |
| KNO$_3$ | 950.00 |
| KH$_2$PO$_4$ | 170.00 |
| MgSO$_4$•7H$_2$O | 925.00 |
| CaCl$_2$•2H$_2$O | 11.00 |
| Minor | |
| KI | 4.1500 |
| H$_3$BO$_3$ | 31.0000 |
| ZnSO$_4$•7H$_2$O | 43.0000 |
| MnSO$_4$•H$_2$O | 21.0000 |
| Na$_2$MoO$_4$•2H$_2$O | 1.3000 |
| CuSO$_4$•5H$_2$O | 0.5000 |
| CoCl$_2$•6H$_2$O | 0.1300 |
| Iron | |
| FeSO$_4$•7H$_2$O | 27.8 |
| Na$_2$EDTA | 37.2 |
| Vitamins | |
| Thiamine-HCl | 0.1000 |
| Pyridoxine-HCl | 0.1000 |
| Nicotinic acid | 0.5000 |
| Myo-Inositol | 100 |

TABLE 6

Effect of carbon source on radiata pine induction success

| Treatment | % induction | % cryopreserved | Embryo yield (#SE/gFW) |
|---|---|---|---|
| MSG | 10.03 | 100 | 213 |
| TXR | 26.07 | 100 | 405 |

Example 7

Effect of Carbon Source on Somatic Embryo Development of Radiata Pine Embryos in Liquid Cultures Tissue induced on MSG containing sucrose was further maintained on MSG sucrose medium, and tissue induced on TXR galactose was maintained on TXR medium containing galactose as described in Example 6. The tissue morphology of the lines induced on galactose was different from that induced on sucrose. Tissue induced on galactose-containing medium consisted of more early stage immature embryos and a limited amount of suspensor type of surrounding tissue, whereas predominantly suspensor type tissue and very few embryos were observed in the tissue induced on sucrose. The lines used in this study were RP1, RP2, RP3, and RP4.

Suspension cultures were initiated as described in Example 6. These cultures were maintained in liquid media for 20-28 days by transfers to fresh maintenance medium every 10 to 14 days. Up to five fold increase of the tissue was estimated at the end of each 10 to 14 day transfer.

In order to study the effect of galactose on embryo development after the proliferation stage, 2 g tissue was further transferred to 250 ml flasks, containing 50 ml of TXR prematuration medium I supplemented with either 1.0% sucrose or 3.0% galactose. As with loblolly pine cultures, prematuration I requires reduction of hormones either by reducing the auxin and cytokinin concentrations to optimally about 1/20 of the concentration of proliferation step, or by adding charcoal at about 0.01 to 1%, or a combination of both.

After the 10-14 day period, 1.5 g tissue was transferred to 250 ml flasks containing 50 ml TXR prematuration medium II to which either 1.0% sucrose or 3.0% galactose and 90 µM ABA were added.

Early stage somatic embryos were collected after 10 to 14 days and matured on modified 1/2 LV maturation medium as described in Example 6. Results are shown in Table 7.

TABLE 7

Tissue and somatic embryo yield.

| Carbon source | Grams FW at the end of proliferation stage (from 1.5 g) | # SE/g FW ± sd |
|---|---|---|
| Sucrose | 11.05 ± 2 | 213.3 ± 6 |
| Galactose | 9.5 ± 2 | 405.3 ± 10 |

Tissue growth increased more than 5 times when galactose was used as a carbon source and the number of mature somatic embryos at the end of maturation was doubled.

Examples Assessing Douglas Fir Somatic Embryogenesis

The culture medium for Douglas fir was TX medium (see Table A) with the following additives: glutamine 100 mg., Casein hydrolysate 100 mg., and pH 5.8. The following compounds were added into the basal medium for Douglas fir somatic embryo development at different stages:

1) Induction medium: 18 µM 2,4-D and 9 µM BA, phytagel 0.28%, sucrose 1%
2) Solid maintenance medium: 9 µM 2,4-D and 4.5 µM BA, phytagel 0.28%, sucrose 1%.
3) Liquid maintenance and bulking-up medium: 9 µM 2,4-D and 4.5 µM BA, different carbon sources for experiments.
4) Liquid pre-treatment medium: 20 (first week) or 30 µM ABA (second week), 10% PEG4000 (first week) or PEG1500 (second week), different carbon sources as described in examples below.
5) Solid maturation media: TX (Table A) plus 0.02% NH$_4$NO$_3$
   Medium I. 40 µM ABA, 10% PEG 1500, maltose 2.5%, phytagel 0.6%
   Medium II. 60 µM ABA, 10% PEG1500, maltose 2.5% and sucrose 1%, phytagel 0.8%
   Medium III. 70 µM ABA, 6% PEG1500, sucrose 6%, phytagel 1%.

Embryogenic tissue was induced from immature zygotic embryos. The cones and seeds were surface-sterilised as described for pines, and embryos were dissected out from megagametophytes. The embryos, with the attachment of suspensors to their megagametophytes, were placed on the surface of induction medium. The culture was kept in darkness at 23° C. Embryogenic tissue was sub-cultured once every two weeks onto solid maintenance medium.

Example 8

Effects of Carbohydrates on Liquid Maintenance of Douglas Fir Embryogenic Tissue Embryogenic tissue of Douglas fir was collected from solid maintenance culture and one gram of tissue was transferred into a 200 ml flask containing 50 ml TX (see Table A) liquid maintenance medium. The liquid maintenance medium was supplied with different sugars (Table 8).

TABLE 8

Growth of Douglas fir tissue (fold, mean ± SD) in suspension maintenance/bulking-up cultures for 3 weeks.
Cell line DF-2 was used in this experiment.

| Major carbon sources | Additional glucose (%) | Tissue growth |
|---|---|---|
| 0.5% galactose | 0 | 68.64 ± 4.58 |
| 0.5% galactose | 0.025 | 97.02 ± 2.67 |
| 1% lactose | 0 | 1.40 ± 0.14 |
| 1% lactose | 0.025 | 2.75 ± 0.24 |
| 0.5% mannitol | 0 | 1.60 ± 0.13 |
| 0.5% mannitol | 0.025 | 3.34 ± 0.22 |
| 0.5% glucose | 0 | 223.14 ± 15.4 |
| 1% sucrose | 0 | 100.94 ± 12.0 |
| 1% maltose | 0 | 85.01 ± 1.71 |

The tissue was drained, weighed and sub-cultured once per week. During a culture period of three weeks, the highest tissue growth was found in the culture with glucose as the major carbon source. The media containing sucrose, maltose and galactose also supported a fast tissue growth. With these latter sugars, tissue increased to 68 to 100 fold in three weeks. Tissue grew little in the media containing lactose or mannitol. Supplement of a small amount of glucose in the media containing galactose, lactose or mannitol respectively increased tissue growth (Table 8) and this increase of tissue growth corresponded to the amount of glucose supplied into the media (data not shown). Similar results were obtained within two cell lines, DF-7A and DF-2.

Thus, among the tested sugars, glucose resulted in the fastest tissue growth. Sucrose, maltose and galactose were all good carbon sources for tissue growth. Lactose and mannitol have to be used in combination with other carbon sources such as glucose, in order to achieve a good tissue growth.

Example 9

Osmolarity and Carbon Metabolism in Liquid Maintenance

After a one-week liquid maintenance culture, the osmolarity of culture medium showed little change when lactose or mannitol was used as the major carbon source while the medium containing either galactose or glucose decreased from 22% to 32% (Table 9). More change of medium osmolarity occurred during week 2 than week 1. The medium osmolarity changed little when lactose or mannitol was used in the media.

TABLE 9

Medium osmolarity (mmol/kg, mean ± SD) and changes before and after a one-week tissue inoculation.

| Carbohydrates | Osmolarity before inoculation | Osmolarity after inoculation | Change (%) |
|---|---|---|---|
| 0.5% galactose | 71.67 ± 1.15 | 48.67 ± 0.58 | −32.09 |
| 1% lactose | 93.33 ± 0.58 | 94.67 ± 1.15 | 1.44 |
| 0.5% mannitol | 76 ± 1 | 71.67 ± 1.15 | −5.70 |
| 0.5% glucose | 77.67 ± 0.58 | 54.67 ± 1.53 | −29.61 |

Sugars in the media were quantified with the method of enzymatic BioAnalysis that can quantify the specific carbohydrates in trace amount. In the medium, glucose decreased sharply, up to 94.4%, while galactose decreased about 80.6%. Little changes were found with lactose or mannitol after a one-week culture (Table 10).

TABLE 10

Changes of carbohydrates in Douglas fir suspension media after tissue (DF-7A), inoculation for one week.

| Major carbon source | Sugar analyzed | Before use (%) | After use (%) | Decreased (%) |
|---|---|---|---|---|
| 0.5% glucose | Glucose | 0.5 | 0.0278 | 94.44 |
| 0.5% galactose | Galactose | 0.5 | 0.097 | 80.6 |
| 1% lactose | Lactose | 1 | 0.99 | 0.01 |
| 0.5% mannitol | Mannitol | 0.5 | 0.5 | 0 |

The results of this study show that glucose is an easily-consumable carbon source for Douglas fir tissue. Galactose can be utilised slowly. Lactose and mannitol are not metabolised by Douglas fir tissue.

Example 10

Effects of Carbohydrates in Suspension Cultures on Embryo Yield

In pre-treatment media, ABA was the only plant hormone present in the media and polyethylene glycol (PEG) was added as a non-permeable osmoticum to stimulate and synchronize embryo maturation. It was a common phenomenon that tissue grew more after being transferred from maintenance media containing other carbon sources into the pre-treatment medium containing maltose as the major carbon source. Tissue grew faster during the first week and then slowed down in the second week (Table 11).

After pre-treatment, about 0.1 g tissue was plated onto a piece of filter paper on the surface of solid maturation medium I. After two weeks, the tissue was transferred with the filter paper to medium II and then medium III after three additional weeks. The maturation culture was kept in darkness, 23° C. for 8 weeks and then 12° C. for one week. Embryos were evaluated after this nine-week maturation. During evaluation only mature embryos with a normal shape and at least three well-developed cotyledons were scored.

TABLE 11

Douglas fir tissue growth (fold, mean ± SD) during pre-maturation treatments (pt) and embryo maturation.

| Carbon source in maintenance & pre-treatment | Growth - Pt week 1 | Growth - Pt week 2 | Total growth | Mature embryos/pp | Yield of embryos (started with one gram of tissue at P1) |
|---|---|---|---|---|---|
| A* & A | 4.9 ± 0.28 | 2.4 ± 0.28 | 11.76 | 75 ± 23.3 | 8017 |
| A & m** | 7.1 ± 0.85 | 2.3 ± 0.14 | 16.33 | 105 ± 27.81 | 15586 |
| B & B | 4.75 ± 1.06 | 1.9 ± 0.28 | 9.025 | 61.38 ± 19.64 | 5035 |
| B & m | 7.7 ± 0.74 | 2.4 ± 0.6 | 18.48 | 82.33 ± 12.5 | 13830 |

TABLE 11-continued

Douglas fir tissue growth (fold, mean ± SD) during pre-maturation treatments (pt) and embryo maturation.

| Carbon source in maintenance & pre-treatment | Growth - Pt week 1 | Growth - Pt week 2 | Total growth | Mature embryos/pp | Yield of embryos (started with one gram of tissue at P1) |
|---|---|---|---|---|---|
| C & C | 6.85 ± 0.64 | 2 ± 0.8 | 13.7 | 53 ± 25.23 | 6600 |
| C & m | 8.5 ± 0.62 | 2.2 ± 0.4 | 18.7 | 96.75 ± 20.65 | 16446 |
| D & D | 9.9 ± 0.57 | 2.3 ± 0.21 | 22.77 | 62 ± 15.4 | 12834 |
| D & m | 9.4 ± 0.6 | 2.4 ± 0 | 22.56 | 105.75 ± 20.36 | 21686 |
| Suc & m | 6.6 ± 0.2 | 4.92 ± 0.28 | 32.472 | 50.5 ± 19.27 | 14906 |

*A: 0.5% galactose, B: 0.5% galactose + 0.01% glucose, C: 0.5% galactose + 0.025% glucose, D: 0.5% galactose + 0.05% glucose
**m - 1% maltose, suc - 1% sucrose, Galactose and a small amount of glucose supplement in liquid maintenance culture combined with maltose in pre-treatment showed the highest embryo yield either in the total number or on the yield per gram of tissue.

The invention claimed is:

1. A method for reproducing coniferous somatic embryos by somatic embryogenesis comprising
growing on a nutrient medium an immature embryogenic culture derived from an explant, the nutrient medium selected from the group consisting of induction medium, maintenance medium and prematuration medium, and the nutrient medium comprising lactose,
wherein the coniferous somatic embryos are *Pinus taeda* somatic embryos or hybrids thereof, and
wherein when the nutrient medium is the induction medium, growing the immature embryonic culture comprises inducing the explant to form an embryogenic tissue,
wherein when the nutrient medium is the maintenance medium, growing the immature embryonic culture comprises, growing and maintaining the embryogenic culture, and
wherein when the nutrient medium is the prematuration medium, growing the immature embryonic culture further comprises transferring the embryogenic culture from the prematuration medium to maturation medium for subsequent development of mature embryos capable of germination.

2. The method of claim 1, wherein the lactose is less than 6.0% (w/v) of the nutrient medium.

3. The method of claim 1, wherein the nutrient medium is gelled or liquid.

4. The method of claim 1, wherein the nutrient medium is the maintenance medium, wherein the maintenance medium comprises an auxin and a cytokinin, and wherein growing the immature embryonic culture further comprises transferring the embryonic culture from the maintenance medium to a prematuration medium containing less auxin and less cytokinin than the maintenance medium.

5. The method of claim 1, wherein when the nutrient medium is the prematuration medium, and wherein the prematuration medium further comprises abscisic acid.

6. The method of claim 1, wherein the nutrient medium further comprises an additional sugar.

7. The method of claim 6, wherein the additional sugar is readily metabolized.

8. The method of claim 7, wherein the additional sugar is selected from the group consisting of sucrose, glucose, and fructose.

9. The method of claim 1, wherein the immature embryogenic culture contains early stage embryos.

10. The method of claim 1, wherein the lactose is less than 2.0% (w/v) of the nutrient medium.

11. The method of claim 1, wherein the lactose is between 1.0% (w/v) and 6.0% (w/v) of the nutrient medium.

12. The method of claim 1, wherein the nutrient medium further comprises an auxin and a cytokinin.

13. A method for reproducing conifers by somatic embryogenesis which comprises:
growing *Pinus taeda* conifer cells on a nutrient medium comprising lactose, an auxin, and a cytokinin to produce an immature embryogenic culture; and
transferring the immature embryogenic culture to maturation medium to obtain mature embryos capable of germination and reproduction of conifer.

14. The method of claim 13, wherein the nutrient medium further comprises an additional sugar.

15. The method of claim 6, wherein the lactose comprises less than 2% (w/v) of the nutrient medium.

16. The method of claim 6, wherein the lactose is between 1% (w/v) and 2% (w/v) of the nutrient medium.

17. The method of claim 6, wherein the lactose is less than 6% (w/v) of the nutrient medium.

18. A method for reproducing somatic embryos by somatic embryogenesis comprising
growing on a nutrient medium an immature embryogenic culture derived from an explant, the nutrient medium selected from the group consisting of maintenance medium and prematuration medium; and the nutrient medium comprising lactose;
wherein the coniferous somatic embryo is selected from the group consisting of *Pinus taeda* or hybrids thereof, *Pinus radiata* or hybrids thereof and *Pseudotsuga menziesii* or hybrids thereof, and
wherein when the nutrient medium is the maintenance medium growing the immature embryogenic culture comprises growing and maintaining the embryogenic culture, and
wherein when the nutrient medium is the prematuration medium, growing the immature embryonic culture further comprises transferring the embryogenic culture from the prematuration medium to maturation medium for subsequent development of mature embryos capable of germination.

19. The method of claim 18, wherein the coniferous somatic embryo is *Pinus radiata* or a hybrid thereof.

20. The method of claim 18, wherein the coniferous somatic embryo is *Pseudotsuga menziesii* or a hybrid thereof.

21. The method of claim 18, wherein the lactose comprises less than 2% (w/v) of the nutrient medium.

22. The method of claim 18, wherein the lactose is between 1% (w/v) and 2% (w/v) of the nutrient medium.

23. The method of claim 18, wherein the lactose is less than 6% (w/v) of the nutrient medium.

24. The method of claim 18, wherein the nutrient medium further comprises an additional sugar.

25. A method for reproducing conifers by somatic embryogenesis which comprises:

growing *Pinus taeda* conifer cells on a nutrient medium comprising lactose, an auxin, and a cytokinin to produce an immature embryogenic culture; and transferring the immature embryogenic culture to maturation medium to obtain mature embryos capable of germination and reproduction of conifers, wherein the maturation medium does not contain of auxin.

26. The method of claim 25, wherein the somatic embryo is *Pinus radiata* or a hybrid thereof.

27. The method of claim 25, wherein the somatic embryo is *Pseudotsuga menziesii* or a hybrid thereof.

28. The method of claim 25, wherein the maturation medium further does not contain cytokinin.

29. The method of claim 25, wherein the nutrient medium further comprises an additional sugar.

* * * * *